US 6,489,501 B2
(12) United States Patent
Schattenmann

(10) Patent No.: US 6,489,501 B2
(45) Date of Patent: Dec. 3, 2002

(54) METHOD AND APPARATUS FOR FORMING A CARBON-SILICON BOND IN A SILANE

(75) Inventor: Florian Johannes Schattenmann, Ballston Lake, NY (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/792,337

(22) Filed: Feb. 26, 2001

(65) Prior Publication Data

US 2002/0161254 A1 Oct. 31, 2002

(51) Int. Cl.$^7$ .................................................. C07F 7/08
(52) U.S. Cl. ........................................ 556/478; 556/481
(58) Field of Search .................... 556/478, 481

(56) References Cited

U.S. PATENT DOCUMENTS 2,380,995 A    8/1945   Rochow
6,258,971 B1 *  7/2001   Schattenmann ............. 556/478

FOREIGN PATENT DOCUMENTS

| DE | 2332167   | 6/1973  |
| DE | 3821483 A | 12/1989 |
| DE | 3821483 C | 4/1996  |
| GB | 2013207   | 8/1979  |

OTHER PUBLICATIONS

Bazan et al., "Organosilicon Compounds", vol. 2, part 1, Academic Press, NY, 1965, pp. 105, 108, 109, 300, 305, 307.*
G.B. Goodwin, et al., Adv. Chem. Ser. 224–251 (1990).
A. Boudin et al., Organometallics 7, 1165–71 (1988).
A. Boudin et al., J. Organomet. Chem. 362, 265–72 (1989).
A. Boudin et al., Angew. Chem. Int. Ed. Engl. 25, 474 (1986).

* cited by examiner

Primary Examiner—Paul F. Shaver
(74) Attorney, Agent, or Firm—Bernadette M. Bennett; Noreen C. Johnson

(57) ABSTRACT

A method for forming at least one product silane, comprising reacting a transition metal hydride with a starting silane in a presence of a catalyst and at a temperature that exceeds a threshold temperature associated with said reacting.

20 Claims, 1 Drawing Sheet

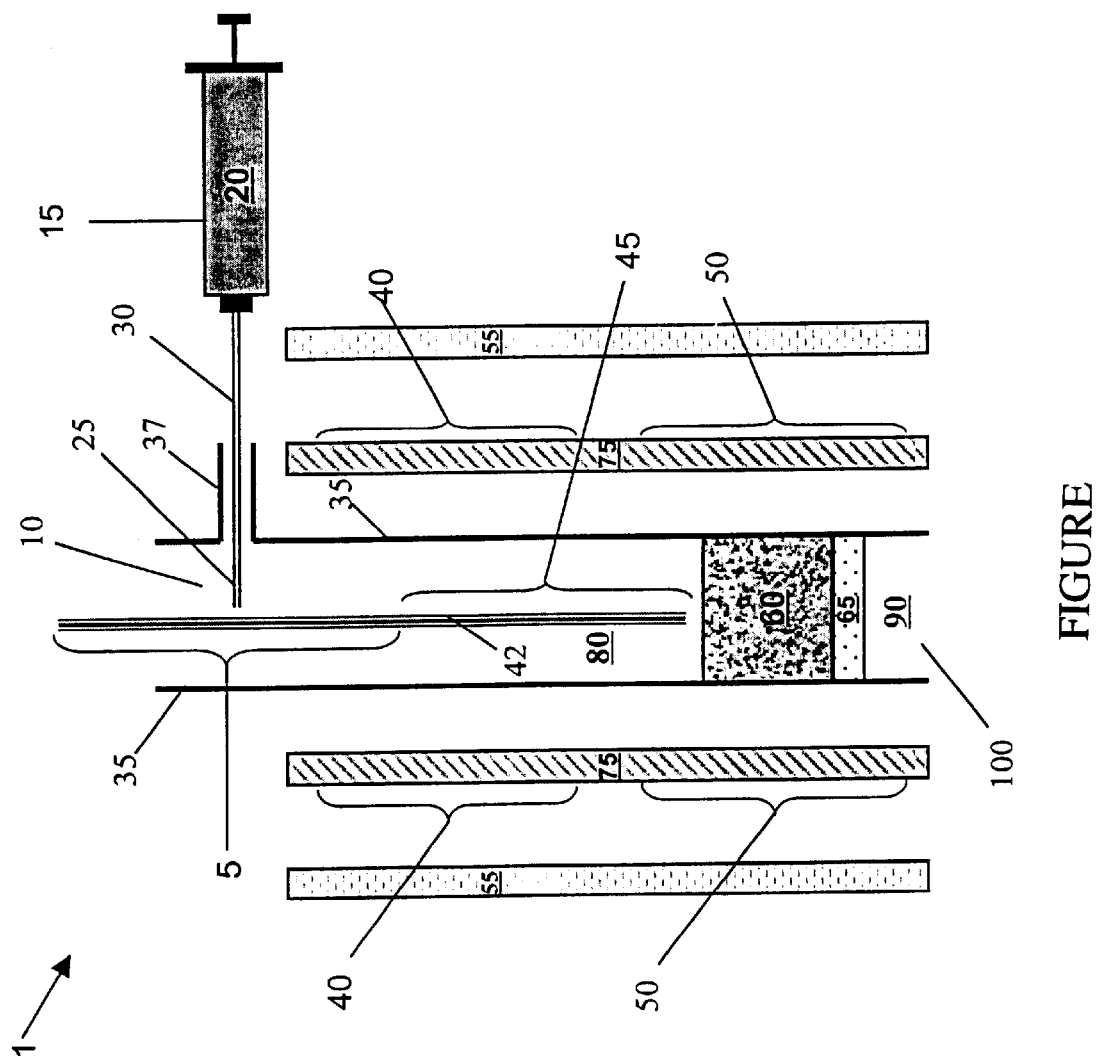
FIGURE

METHOD AND APPARATUS FOR FORMING A CARBON-SILICON BOND IN A SILANE

STATEMENT REGARDING FEDERALLY SPONSORED RESEARCH & DEVELOPMENT

The government may have certain rights in this invention pursuant to contract number DE-FC02-98CH10931 awarded by the United States Department of Energy.

BACKGROUND OF THE INVENTION

The present invention relates to a method and apparatus for forming at least one silicon-carbon bond in a silane.

Methyl chlorosilanes are typical starting materials used commercially in the manufacture of silicone polymers. Methyl chlorosilanes, comprising a silicon-carbon bond, are formed in a reaction between methyl chloride and elemental silicon, first disclosed by Rochow in 1945 in U.S. Pat. No. 2,380,995. However, the Rochow reaction relies on a costly energy consuming reduction of silicon dioxide to elemental silicon. Thus, there is a need for a method and apparatus for forming silicon-carbon bonds that avoids using the costly energy consuming reduction of silicon dioxide to elemental silicon.

BRIEF SUMMARY OF THE INVENTION

The present invention provides a method for forming at least one product silane, comprising reacting a transition metal hydride with a starting silane in a presence of a catalyst and at a temperature that exceeds a threshold temperature associated with said reacting, wherein the starting silane has a chemical form of $T_n Si(OR)_{(4-n)}$, wherein the at least one product silane includes at least one silicon-carbon bond that is not present in the starting silane, wherein each T is independently a hydrogen atom or a monovalent hydrocarbon group, wherein each R independently includes a monovalent hydrocarbon group, and wherein n is an integer in a range between 0 and about 3.

In addition, the present invention provides a product silane having the chemical form of $(R_m)(T_n)Si(OR)_{(4-m-n)}$, wherein each T independently includes a monovalent hydrocarbon group, wherein each R independently includes a hydrocarbon group, and wherein n is an integer in a range between 0 and about 3, wherein m is an integer in a range between about 1 and about 4−n, wherein the product silane is formed by the process of endothermically reacting a transition metal hydride with a starting silane in a presence of a catalyst and at a temperature that exceeds a threshold temperature associated with said reacting, and wherein the starting silane has a chemical form of $(R_{m-1})(T_n)Si(OR)_{(5-m-n)}$.

DESCRIPTION OF THE DRAWINGS

The FIGURE depicts an apparatus for reacting a transition metal hydride with a starting silane to form a product silane having at least one silicon-carbon bond.

DETAILED DESCRIPTION OF THE INVENTION

The present invention provides a method for forming at least one silicon-carbon bond in a silane. The method of the present invention does not require a reduction of silicon dioxide to elemental silicon. A transition metal hydride is reacted with a starting silane in the presence of a catalyst to yield a product mixture. The starting silane includes a silicon-oxygen bond. The product mixture includes a product silane and the product silane includes at least one silicon-carbon bond that is not present in the starting silane. The catalyst may include, for example, a fluoride. The aforementioned chemical reaction is endothermic and a minimum temperature, hereinafter referred to as "threshold temperature", is required for the reaction to yield a measurable amount of the product silane. The chemical reaction takes place at a temperature, hereinafter referred to as "effective temperature", that is equal to or greater than the threshold temperature.

The starting silane is of the form $T_n Si(OR)_{(4-n)}$, where n=0, 1, 2, or 3. $T_n$ exists only for n=1, 2, or 3; i.e, $T_0$ does not exist. Similarly, $(OR)_0$ does not exist. Each T independently represents a hydrogen atom or monovalent hydrocarbon group such as alkyl groups, aryl groups, aralkyl groups, alkaryl groups, cycloalkyl groups, bicycloalkyl groups, alkenyl groups, alkalkenyl groups, and alkenylalkyl groups, alkynyl groups, alkalkynyl groups, alkynylalkyl groups, trifluoropropyl groups, cyanopropyl groups, acryloyl groups, arylacryloyl groups, acryloylaryl groups, alkylacyl groups, arylacyl groups alkylenylacyl groups and alkynylacyl groups. Note that any T in the starting silane may be the same as, or differ from, any other T in the starting silane. As an example, if n=2 then $T_n$ includes the two groups $T_1$ and $T_2$, wherein either $T_1=T_2$, or $T_1 \ne T_2$ applies. Each R independently represents a monovalent hydrocarbon group as described above. Similarly, any R in the starting silane may be the same as, or differ from, any other R in the starting silane. As another example, if n=2 then $(OR)_{4-n}$ includes two groups $OR_1$ and $OR_2$, wherein either $R_1=R_2$, or $R_1 \ne R_2$ applies. Also note that any T may be the same as or may differ from any R in the starting silane.

The term "alkyl group" designates both normal alkyl and branched alkyl groups. Included among normal and branched alkyl groups are those having carbon atoms in a range between about 1 and about 22. Normal alkyl and branched alkyl groups include, for example: methyl, ethyl, propyl, isopropyl, butyl, tertiary-butyl, pentyl, neopentyl, hexyl, octyl, decyl, dodecyl groups. Aryl groups include, for example, phenyl, anthryl and phenanthryl groups. Included among aralkyl groups are those having carbon atoms in a range between about 7 and about 14. Aralkyl groups include, for example: benzyl, phenylbutyl, phenylpropyl, phenylethyl and phenylallyl groups. Alkaryl groups include, for example, tolyl and cumyl groups. Cycloalkyl or bicycloalkyl groups each include ring carbon atoms in a range between about 3 and about 12, and no greater than about 50 carbon atoms totally. Cycloalkyl groups include, for example: cyclobutyl, cyclopentyl, cyclohexyl, methylcyclohexyl, and cycloheptyl groups. Bicycloalkyl groups include, for example: norbornyl. Alkenyl groups include, for example: ethenyl, butenyl and propargyl groups. Alkenylalkyl groups include for example: allyl groups. Alkylalkenyl groups include for example: 4-methyl-3-butenyl. Alkenylphenyl groups include for example: vinylphenyl groups. Arylalkenyl groups include for example: styryl groups. Alkynyl groups include for example: ethynyl groups. Alkynylalkyl groups include for example: propargyl groups. Alkylalkynyl groups include for example: 4-methyl-3-butynyl groups. Acryloyl groups include for example: acryloyl and methacryloyl groups. Arylacryloyl groups include for example: phenylacryloyl groups. Acryloylaryl groups include for example: acryloylphenyl and methacryloylphenyl groups. Acyl and alkylacyl groups include for example: formyl, acetyl, propanoyl, butanoyl, pentanoyl, hexanoyl, heptanoyl, octanoyl, isopropanoyl, isobutanoyl, isopentanoyl, neopentanoyl, 2-methylpentanoyl, 3-methylpentanoyl, 2-methylhexanoyl, 3-methylhexanoyl, t-butanoyl. Arylacyl groups include for example: phenylacetyl, anthrylacetyl, phenanthrylacetyl. Alkenylacyl groups include for example: acryloyl and methacryloy. Alkynylacyl groups include for example: propynoyl, butynoyl, pentynoyl and hexynoyl.

As an example, the starting silane may include tetramethoxysilane, wherein n is 0 and R is $CH_3$ such that $(OR)_4$ is $(OCH_3)_4$. Alternatives to tetramethoxysilane include, for example: any tetraalkoxysilanes (e.g., tetraethoxysilane, tetrapropoxysilane, etc.); tetraisopropoxysilane; tetraaryloxysilanes (e.g., tetraphenoxysilane); and tetra(alkoxyaryloxy)silanes (e.g., dimethoxydiphenoxysilane). The level of purity of the tetraalkoxysilane is at least about 80% by weight.

Starting silanes where T is a hydrogen atom may include trimethoxysilane, $HSi(OCH_3)_3$, which corresponds to n=1 and $R=CH_3$ such that $(OR)_{(4-n)}=(OCH_3)_3$. Alternatives to trimethoxysilane include, for example: any trialkoxysilanes (e.g., triethoxysilane, tripropoxysilane, etc.); triisopropoxysilane; triaryloxysilanes (e.g., triphenyloxysilane); and tri-(alkoxyaryloxy)silanes (e.g., methoxydiphenyloxysilane). The level of purity of the trialkoxysilane is at least about 80% by weight.

Given the starting silane is of the form $T_nSi(OR)_{(4-n)}$, the first product silane is of the form $(R)(T_n)Si(OR)_{(3-n)}$. Thus, the chemical reaction of the present invention generates the silicon-carbon bond in the form R—Si in the product silane. Since the product silane constitutes a chemical rearrangement of the R groups of the starting silane, the R groups in the product silane are the same as the corresponding R groups in the starting silane. Additionally, the T groups in the product silane are the same as the corresponding T groups in the starting silane.

For notational purposes, let X denote the starting silane $T_nSi(OR)_{(4-n)}$. The product silane $(R)(T_n)Si(OR)_{(3-n)}$ can be considered as a first product silane denoted as $Z_1$. Note that if $n \leq 2$, $Z_1$ can itself react with the transition metal hydride to generate a second product silane $(R_2)(T_n)Si(OR)_{(2-n)}$ denoted as $Z_2$. Similarly if $n \leq 1$, $Z_2$ can react with the transition metal hydride to generate a third product silane $(R_3)(T_n)Si(OR)_{(1-n)}$ denoted as $Z_3$. Additionally if n=0, then $T_n$ does not exist and $Z_3$ can react with the transition metal hydride to generate a fourth product silane $(R_4)Si$ denoted as $Z_4$. Thus, the product mixture potentially includes $Z_1$, $Z_2$, $Z_3$, and $Z_4$. The relative amounts of $Z_1$, $Z_2$, $Z_3$, and $Z_4$ in the product mixture depends on the total time of the chemical reactions and on the reaction rates associated with conversion of X to $Z_1$, $Z_1$ to $Z_2$, $Z_2$ to $Z_3$, and $Z_3$ to $Z_4$. The reaction rates depend on the effective temperature, the catalyst, and other factors such as a degree to which the reactants are uniformly distributed. Thus, the preceding variables (time of reaction, effective temperature, etc.) can be adjusted to maximize a yield of any one of $Z_1$, $Z_2$, $Z_3$, and $Z_4$. For example, it may be desired to optimize the yield of $Z_2$ in conjunction with a given application if the product silane having two silicon-carbon bonds and two silicon-oxygen bonds is commercially valuable in the given application.

The present invention produces a product silane having the chemical form of $(R_m)(T_n)Si(OR)_{(4-m-n)}$. Each T and each R independently includes a monovalent hydrocarbon group as stated above. Note that n is an integer in a range between 0 and about 3, and m is an integer in a range between about 1 and about 4−n. Thus, the product silane $(R_m)(T_n)Si(OR)_{(4-m-n)}$ is formed by the process of endothermically reacting a transition metal hydride with a first starting silane in a presence of a catalyst and at a temperature that exceeds the threshold temperature of said reacting. The first starting silane has a chemical form of $(R_{m-1})(T_n)Si(OR)_{(5-m-n)}$.

The following list of starting silanes and product silanes exemplify the aforementioned chemical structures. If the starting silane is tetramethoxysilane, then the product silane may include methyltrimethoxysilane, dimethyldimethoxysilane, trimethylmethoxysilane, and tetramethylsilane. If the starting silane is methlytrimethoxysilane, then the product silane may include dimethyldimethoxysilane, trimethylmethoxysilane, and tetramethylsilane. If the starting silane is tetraethoxysilane, then the product silane may include ethyltriethoxysilane, diethyldiethoxysilane, triethylethoxysilane, and tetraethylsilane. If the starting silane includes tetrapropoxysilane, then the product silane is propyltripropoxysilane, dipropyldipropoxysilane, tripropylpropoxysilane, and tetrapropylsilane. In Table 1, the aforementioned product silanes are grouped according to their respective starting silane. For example, the product silanes from tetramethoxysilane are grouped with tetramethoxysilane. Note that the first product silane in the group of product silanes from tetramethoxysilane, namely methyltrimethoxysilane, was formed from tetramethoxysilane, as demonstrated in Examples 1–4. Likewise, the first product in the group of product silanes from methyltrimethoxysilane, namely dimethyldimethoxysilane, was formed from methyltrimethoxysilane, as demonstrated in Example 7. Similarly, the first product in the group of product silanes from tetraethoxysilane, namely ethyltrimethoxysilane, was formed from tetraethoxysilane, as demonstrated in Example 5. Additionally, the first product in the group of product silanes from tetrapropoxysilane, namely propyltripropoxysilane, was formed from tetrapropoxysilane, as demonstrated in Example 6. If the starting silane is trimethoxysilane, $HSi(OCH_3)_3$, then the product silane may include methyltrimethoxysilane, dimethyldimethoxysilane, trimethylmethoxysilane, and tetramethylsilane.

TABLE 1

| Starting Silane [$(T_n)Si(OR)_{4-n}$] | | | | Product Silane [$(R_m)(T_n)Si(OR)_{4-n-m}$] | | | | |
| --- | --- | --- | --- | --- | --- | --- | --- | --- |
| Formula | T | R | n | Formula | T | R | n | m |
| $Si(OCH_3)_4$ | Absent | $CH_3$ | 0 | $(CH_3)Si(OCH_3)_3$* | Absent | $CH_3$ | 0 | 1 |
| | | | | $(CH_3)_2Si(OCH_3)_2$ | Absent | $CH_3$ | 0 | 2 |
| | | | | $(CH_3)_3Si(OCH_3)$ | Absent | $CH_3$ | 0 | 3 |
| | | | | $(CH_3)_4Si$ | Absent | $CH_3$ | 0 | 4 |

TABLE 1-continued

| Starting Silane [$(T_n)Si(OR)_{4-n}$] | | | | Product Silane [$(R_m)(T_n)Si(OR)_{4-n-m}$] | | | | |
|---|---|---|---|---|---|---|---|---|
| Formula | T | R | n | Formula | T | R | n | m |
| $(CH_3)Si(OCH_3)_3$ | $CH_3$ | $CH_3$ | 1 | $(CH_3)_2Si(OCH_3)_2$* | $CH_3$ | $CH_3$ | 1 | 1 |
| | | | | $(CH_3)_3Si(OCH_3)$ | $CH_3$ | $CH_3$ | 1 | 2 |
| | | | | $(CH_3)_4Si$ | $CH_3$ | $CH_3$ | 1 | 3 |
| $(CH_3)_2Si(OCH_3)$ | $CH_3$ | $CH_3$ | 2 | $(CH_3)_3Si(OCH_3)$ | $CH_3$ | $CH_3$ | 2 | 1 |
| | | | | $(CH_3)_4Si$ | $CH_3$ | $CH_3$ | 2 | 2 |
| $Si(C_2H_5O)_4$ | Absent | $C_2H_5$ | 0 | $(C_2H_5)Si(OC_2H_5)_3$* | Absent | $C_2H_5$ | 0 | 1 |
| | | | | $(C_2H_5)_2Si(OC_2H_5)_2$ | Absent | $C_2H_5$ | 0 | 2 |
| | | | | $(C_2H_5)_3Si(OC_2H_5)$ | Absent | $C_2H_5$ | 0 | 3 |
| | | | | $(C_2H_5)_4Si$ | Absent | $C_2H_5$ | 0 | 4 |
| $Si(C_3H_7O)_4$ | Absent | $C_3H_7$ | 0 | $(C_3H_5)Si(OC_3H_7)_3$* | Absent | $C_3H_7$ | 0 | 1 |
| | | | | $(C_3H_7)_2Si(OC_3H_7)_2$ | Absent | $C_3H_7$ | 0 | 2 |
| | | | | $(C_3H_7)_3Si(OC_3H_7)$ | Absent | $C_3H_7$ | 0 | 3 |
| | | | | $(C_3H_7)_4Si$ | Absent | $CH_3$ | 0 | 4 |

A product silane having an asterisk (*) denotes a first product silane (i.e., $Z_1$). A product silane not having an asterisk denote second, third, or fourth product silanes (i.e., $Z_2$, $Z_3$, $Z_4$).

The transition metal hydride includes, for example, any of the following hydrides or a combination thereof: $TiH_x$, $ZrH_x$, $YH_x$, $YH_3$, $LaH_x$, CuH, and $ZnH_x$, wherein x is a real number greater than 0 and less than or equal to about 2. $ZrH_x$ is typically used commercially as a moderator in nuclear reactors and $TiH_x$ may be used as a high hydrogen density material. Both metal hydrides are stable in dry air. $TiH_x$ decomposes at a temperature in a range between about 400° C. and about 1000° C., and $ZrH_x$ is stable below about 1000° C.

The catalyst may include a metal fluoride salt having a melting point exceeding the threshold temperature such as, for example, potassium fluoride (KF), lithium fluoride (LiF), sodium fluoride (NaF), magnesium fluoride (MgF), cesium fluoride (CsF), and combinations thereof. An alternative catalyst includes: organic amines comprising 4-(dimethylamino)pyridine; phosphine oxides (e.g., triphenylphosphine oxide); and amine N-oxides (e.g., pyridine N-oxide).

The FIGURE is a front cross-sectional view of an apparatus 1 for reacting a starting mixture 60 with a starting silane 20 to produce a product mixture 90. The starting mixture 60 includes a transition metal hydride and a catalyst. The starting silane 20 includes at least one silicon-oxygen bond and may be structured according to the formula $T_nSi(OR)_{(4-n)}$, as discussed above. The product mixture 90 includes the product silane having a silicon-carbon bond. The catalyst may include, for example, a fluoride catalyst.

Referring to the FIGURE, the apparatus 1 includes a fixed bed reactor wherein the fixed bed includes the starting mixture 60. The apparatus 1 comprises: an outer glass jacketed column 55, an inner heated metal wound glass tube 75, and a volumetric enclosure 80 having a boundary 35. The metal wound glass tube 75 has an upper heated section 40 and a lower heated section 50. The volumetric enclosure 80 is within the inner heated metal wound glass tube 75. The reaction of the transition metal hydride of the starting mixture 60 with the starting silane 20 takes place within the volumetric enclosure 80. The volumetric enclosure 80 comprises: a carrier gas inlet 10, a gas tight reagent inlet 37, a porous frit 65, the starting mixture 60 on the porous frit 65, a reaction product outlet 100, and a thermocouple 42 having an upper preheat zone 5 and a lower reacting zone 45. The gas tight reagent inlet 37 comprises a transfer line 30. The transfer line 30 includes a portion 25 extending into the volumetric enclosure 35, and a remaining portion connected to a motorized syringe 15. The motorized syringe 15 includes the starting silane 20.

A carrier gas (e.g., argon, hydrogen, helium, nitrogen) is introduced into the carrier gas inlet 10 causing air from the volumetric enclosure 80, and from the starting mixture 60, to be removed and expelled through the reaction product outlet 100. After the volumetric enclosure 35 and mixture 60 have been purged with carrier gas, the fixed bed reactor 1, including the mixture 60, is heated to an effective temperature in a range between about 350° C. and about 550° C. The motorized syringe 15 effectuates a continuous and controlled delivery of the starting silane 20 into the volumetric enclosure 80. Alternatively, the starting silane 20 could be delivered to the volumetric enclosure 80 manually as well as in a semicontinuous or in a batch mode. The starting silane 20 reacts with the starting mixture 60 at the effective temperature.

Alternatively, the reaction can be performed in other types of reactors, such as stirred bed reactors and fluidized bed reactors. A stirred bed is similar to a fixed except that there is mechanical agitation in the stirred bed to keep the bed in constant motion. In the stirred bed reactor, agitation of the bed facilitates contact of the starting silane 20 with the starting mixture 60 by preventing agglomeration of particles of the starting mixture 60. A fluidized bed reactor, on the other hand, is a bed in which the starting mixture 60 is fluidized; that is, the starting mixture 60 is suspended in a gas (e.g., argon) and mixed with silane 20, such that the gas is passed through the starting mixture 60. The fluidized bed provides the advantages of the stirred bed reactor without using mechanical agitation that may cause particles participating in the reaction to fragment, wherein new surfaces of the fragmented particles may be created that promote unwanted side reactions.

The reaction of the present invention may be performed in batch mode, continuous mode, or semi-continuous mode. With a batch mode reaction, for instance, all of the reactant components are combined and reacted until most of the reactants are consumed. In order to proceed, the reaction has to be stopped and additional reactant added. A fixed bed and stirred bed may both be run under batch conditions. In contrast, a fluidized reactor is typically run under continuous conditions. With continuous conditions, the reaction does not have to be stopped in order to add more reactants.

Products from reaction of the present invention may be isolated by any convenient means. Typically, product(s) may be isolated by condensation into fractions typically referred to as condensate. Products may be purified by any convenient means such as distillation. Once the fractions are collected, the formation of a silane having at least one silicon-carbon bond may be confirmed by such methods as gas chromatography (GC), gas chromatography-mass spectroscopy (GC/MS), and multi-nuclear magnetic resonance spectroscopy (NMR).

The product silanes obtained by the present invention may be used in a variety of applications. For example, the product silanes may be used as: precursors to silicones and organo-functional silicon compounds, precursors to pure and ultra-pure silicon dioxide, coupling agents, additives for plastic applications, and adhesion promoters.

In order that those skilled in the art will be better able to practice the invention, the following seven examples are given by way of illustration and not by way of limitation.

Examples 1–4 were conducted at an effective temperature between about 350° C. and about 600° C. and Examples 5–7 were conducted at an effective temperature between about 250° C. and 350° C. in the fixed bed reactor 1 depicted in the FIGURE. In each Example, fractions of the product mixture 90 were collected and characterized using GC. Examples 1, 2, and 4 show that a silane, methyltrimethoxysilane, was produced, wherein the silane has at least one silicon-carbon bond, according to the embodiments of the present invention. The percentages of product silane in Tables 2–8 refer to percentages in the individual fractions of the collected downstream reactor effluent, including unreacted starting silane 20.

EXAMPLE 1

Titanium hydride [2.0 grams (g); 40 millimole (mmol)] and potassium fluoride (2.0 g; 34 mmol) were intimately mixed and deposited on porous frit 65 to form mixture 60. Air in the starting mixture, as well as in the volumetric enclosure 65 of the fixed bed reactor, was initially purged using argon carrier gas at a rate of 4 milliliters per minute (ml/min, 240 ml/h). Following the initial purge, the rate of carrier gas flow was increased to 20 ml/min. A starting silane of tetramethoxysilane was fed into the carrier gas stream using a motor driven syringe [1.55 milliliters per hour (ml/h); 10 ml total]. The molar ratio of the starting silane 20 to the titanium hydride to the potassium fluoride was about 2:1.2:1. The reactor 1 was heated by a vertical furnace to about 400° C. and maintained at about 400° C. during the course of the chemical reactions. The reactor effluent downstream from the fixed bed was collected in fractions using a water-chilled condenser and analyzed by gas chromatography. Low-boiling components of the reactor effluent that by-passed the water-chilled condenser were collected in a −78° C. trap. Formation of the product silane of methyltrimethoxysilane MeSi(OMe)$_3$ was confirmed by GC, GC/MS, and NMR techniques. Table 2 shows results of Example 1. The percentages of methyltrimethoxysilane [CH$_3$Si(OCH$_3$)$_3$] shown in Table 2 range from 0.78% to 1.29%.

TABLE 2

| Fraction | Fraction Weight (g) | Temperature (° C.) | % CH$_3$Si(OCH$_3$)$_3$ |
|---|---|---|---|
| 1 | 0.92 | 400 | 1.29 |
| 2 | 1.25 | 400 | 0.88 |
| 3 | 1.44 | 400 | 0.82 |
| 4 | 0.72 | 400 | 0.79 |
| 5 | 2.84 | 400 | 0.78 |

EXAMPLE 2

The procedure of Example 1 was followed with the following modifications: cesium fluoride (1.01 g, 6.6 mmol) was substituted for potassium fluoride (2 g, 40 mmol); the initial reactor temperature was about 250° C. and after collecting each fraction, the reactor temperature was increased by 50° C. until the reactor temperature was about 350° C.; the tetramethoxysilane addition rate was about 1.5 ml/h; and instead of Ar, N$_2$ carrier gas was used at a flow rate of about 5 ml/h. Table 3 shows the results of Example 2. The percentage of methyltrimethoxysilane in Table 3 is zero for an initial reactor temperature of 300° C. or less, and 0.68% at an effective temperature of 350° C.

TABLE 3

| Fraction | Fraction Weight (g) | Temperature (° C.) | % CH$_3$Si(OCH$_3$)$_3$ |
|---|---|---|---|
| 1 | 1.19 | 250 | 0 |
| 2 | 0.55 | 300 | 0 |
| 3 | 0.63 | 350 | 0.68 |

EXAMPLE 3

The procedure of Example 1 was followed with the following modifications: titanium hydride on the porous frit 65 instead of a metal fluoride source; the initial reactor temperature was about 250° C. and after collecting each fraction, the reactor temperature was increased in 50° C. increments to a temperature of about 400° C.; the tetramethoxysilane addition rate was about 1.5 ml/h instead of about 1.55 ml/hr; and the argon carrier gas flow rate was about 7.5 ml/h. A total of six fractions were collected, but no methyltrimethoxysilane was measurable.

EXAMPLE 4

The procedure of Example 1 was followed with the following modifications: zirconium hydride (2.0 g, 21.5 mmol) was substituted for titanium hydride (2.0 g, 40 mmol); the weight of KF (1.0 g, 17 mmol) was 50% less than in Example 1; the initial reactor temperature was 300° C. and after collecting each fraction, the reactor temperature was increased in 50° C. increments to about 550° C.; the tetramethoxysilane addition rate was 1.5 ml/h instead of 1.55 ml/h; and instead of Ar, N$_2$ carrier was used at a gas flow rate of 5 ml/h. Table 4 shows the results of Example 4. The percentage of methyltrimethoxysilane in Table 4 is zero for a reactor temperature of 450° C. and less, and 0.75%–0.77at an effective temperature from about 500° C. to about 550° C.

TABLE 4

| Fraction | Fraction Weight (g) | Temperature (° C.) | % CH$_3$Si(OCH$_3$)$_3$ |
|---|---|---|---|
| 1 | 0.80 | 300 | 0 |
| 2 | 0.88 | 350 | 0 |
| 3 | 1.07 | 400 | 0 |
| 4 | 1.02 | 450 | 0 |

TABLE 4-continued

| Fraction | Fraction Weight (g) | Temperature (° C.) | % CH$_3$Si(OCH$_3$)$_3$ |
|---|---|---|---|
| 5 | 0.76 | 500 | 0.75 |
| 6 | 0.97 | 550 | 0.77 |

EXAMPLE 5

The procedure in Example 1 was used with the following modifications: sodium hydride (95% purity, 1.00 g; 39.6 mmol) was substituted for titanium hydride (2.0 g; 40 mmol) a tetraethoxysilane flow rate was about 0.5 ml/h; a tetramethoxysilane flow rate of 2.2 mmol/h; and instead of Ar, N$_2$ carrier gas was used at a flow rate of about 1 ml/min (60 ml/h). The initial reactor temperature was about 250° C. and after collecting a first fraction, the reactor temperature was increased by increments of about 50° C. to a temperature of about 300° C. The weight percent product silane, wherein the product silane was ethyltriethoxysilane, varied from about 1% to about 2.1% as seen in Table 5.

TABLE 5

| Fraction | Fraction Weight (g) | Temperature (° C.) | % CH$_3$Si(OCH$_3$)$_3$ |
|---|---|---|---|
| 1 | 1.10 | 250 | 2.1 |
| 2 | 0.92 | 300 | 1.0 |

EXAMPLE 6

The procedure in Example 1 was used with the following modifications: Sodium hydride (95% purity, 1.00 g; 39.6 mmol) was substituted for titanium hydride (2.0 g; 40 mmol); a tetrapropoxysilane flow rate was about 1.5 ml/h; 5.2 mmol/h instead of a tetramethoxysilane flow rate about 1.55 ml/h, 10 mmol/h; and an argon carrier gas flow rate was about 5 ml/min, 300 ml/h. The reaction was started at about 250° C. and after collection of a first fraction, then increased to about 300° C. until the end of the reaction. The weight percent product silane, wherein the product silane was propyltripropoxysilane, varied from about 0.2% to about 4.4% as seen in Table 6.

TABLE 6

| Fraction | Fraction Weight (g) | Temperature (° C.) | % n-PrSi(O-n-Pr)$_3$ |
|---|---|---|---|
| 1 | 0.71 | 250 | 0.2 |
| 2 | 1.17 | 300 | 1.1 |
| 3 | 1.33 | 300 | 2.7 |
| 4 | 0.67 | 300 | 4.4 |

EXAMPLE 7

The procedure in Example 1 was used with the following modifications: Sodium hydride (95% purity, 1.00 g; 39.6 mmol) was substituted for titanium hydride (2.0 g; 40 mmol); a methyltrimethoxysilane flow rate was about 2.13 ml/h; tetramethoxysilane was used at a flow rate of about 1.55 ml/h, 10 mmol/h; and an argon carrier gas flow rate was about 7.5 ml/min, 450 ml/h. Six fractions were collected while the reactor was maintained at about 350° C. The weight percent product silane, wherein the product silane was dimethyldimethoxysilane, varied from about 2.3% to about 3.3% as can be seen in Table 7.

TABLE 7

| Fraction | Fraction Weight (g) | Temperature (° C.) | % Me$_2$Si(OMe)$_2$ |
|---|---|---|---|
| 1 | 0.85 | 350 | 3.3 |
| 2 | 1.16 | 350 | 3.3 |
| 3 | 0.97 | 350 | 3.1 |
| 4 | 1.02 | 350 | 2.8 |
| 5 | 1.07 | 350 | 2.4 |
| 6 | 0.67 | 350 | 2.3 |

In Example 7, instead of sodium hydride, the hydride could have included other metal hydrides, such as, for example, lithium hydride, potassium hydride, rubidium hydride, cesium hydride, magnesium hydride, calcium hydride, strontium hydride, barium hydride, aluminum hydride, and combinations thereof.

Table 8 identifies the R and T groups and the integer value of n for silanes 20 in Examples 1, 2, and 4–7 above, wherein the R and T groups and the integer value of n relate to the general formula T$_n$Si(OR)$_{4-n}$. Table 8 also identifies the R and T groups for product silanes, wherein the R and T groups for product silanes relate to the general formula (R)T$_n$Si(OR)$_{3-n}$ for Examples 1–7 above.

TABLE 8

| | | Starting silane 20 [T$_n$Si(OR)$_{4-n}$] | | Product Silane [(R)T$_n$Si(OR)$_{3-n}$] | |
|---|---|---|---|---|---|
| Example | n | T | R | T | R |
| 1 | 0 | absent | CH$_3$ | absent | CH$_3$ |
| 2 | 0 | absent | CH$_3$ | absent | CH$_3$ |
| 3 | 0 | absent | CH$_3$ | No Product Silane Was Formed. | |
| 4 | 0 | absent | CH$_3$ | absent | CH$_3$ |
| 5 | 0 | absent | C$_2$H$_5$ | absent | C$_2$H$_5$ |
| 6 | 0 | absent | C$_3$H$_7$ | absent | C$_3$H$_7$ |
| 7 | 1 | CH$_3$ | CH$_3$ | CH$_3$ | CH$_3$ |

An example of a starting silane 20 where T is a hydrogen is HSi(OCH$_3$)$_3$. When HSi(OCH$_3$)$_3$ was passed through a mixture of NaH, (CH$_3$)Si(OCH$_3$)$_3$ was found as a product at temperatures as low as 200° C. as determined by GC analysis. The relative amount of CH$_3$Si(OCH$_3$)$_3$ increased as a function of increasing reactor 1 temperature. At 325° C., 37% of the reactor downstream mixture included (CH$_3$)Si(OCH$_3$)$_3$. Additionally, GC analysis showed the presence of (CH$_3$)$_2$Si(OCH$_3$)$_2$. In the absence of sodium hydride (NaH), HSi(OCH$_3$)$_3$ is thermally stable at temperatures less than 350° C. This result suggests that HSi(OCH$_3$)$_3$ may be an intermediate in a reaction that forms (CH$_3$)Si(OCH$_3$)$_3$ and (CH$_3$)$_2$Si(OCH$_3$)$_2$ from tetramethoxysilane as in Examples 1, 2, 4 above.

While the present invention has been described herein with reference to embodiments, those skilled in the art will understand that various changes may be made and equivalents my be substituted for elements thereof without departing from the scope of the present invention. In addition, many modifications may be made to adapt a particular situation or material to the teachings of the present invention without departing from the essential scope thereof. Therefore, the present invention is not intended to be limited to the particular embodiments disclosed herein for carrying out the present invention. The present invention is intended to include all embodiments falling within the scope of the appended claims.

What is claimed is:

1. A method for forming at least one product silane, comprising reacting a transition metal hydride with a starting silane in a presence of a catalyst and at a temperature that exceeds a threshold temperature associated with said reacting, wherein the starting silane has a chemical form of $T_nSi(OR)_{(4-n)}$, wherein the at least one product silane includes at least one silicon-carbon bond that is not present in the starting silane, wherein each T is independently a hydrogen atom or a monovalent hydrocarbon group, wherein each R independently includes a monovalent hydrocarbon group, and wherein n is an integer in a range between 0 and about 3.

2. The method of claim 1, wherein the catalyst comprises potassium fluoride, cesium fluoride, or combination thereof.

3. The method of claim 1, wherein the catalyst has a melting temperature that does not exceed the threshold temperature.

4. The method of claim 1, wherein the temperature is in a range between about 350° C. and about 600° C.

5. The method of claim 1, wherein the transition metal hydride is selected from the group consisting of $TiH_x$, $ZrH_x$, $HfH_x$, $ScH_x$, $YH_x$, $LaH_x$, CuH, and $ZnH_x$, and combinations thereof, and wherein x is in a range between 0 and about 2.

6. The method of claim 1, wherein each T includes a monovalent hydrocarbon group, wherein n does not exceed 2, and wherein the at least one product silane includes a first product silane having a chemical form of $(R)(T_n)Si(OR)_{(3-n)}$ and a second product silane having a chemical form of $(R_2)(T_n)Si(OR)_{(2-n)}$.

7. The method of claim 6, wherein n does not exceed 1, and wherein the at least one product silane further includes a third product silane having a chemical form of $R_3)(T_n)Si(OR)_{(1-n)}$.

8. The method of claim 7, wherein n equals zero, and wherein the at least one product silane further includes a fourth product silane having a chemical form of $(R_4)Si$.

9. The method of claim 1, wherein the hydrocarbon group is selected from the group consisting of an alkyl group, an aryl group, an aralkyl group, an alkaryl group, an cycloalkyl group, a bicycloalkyl group, and combinations thereof.

10. The method of claim 9, wherein the alkyl group include one of normal and branched alkyl groups, wherein the alkyl group includes carbon atoms in a range between about 1 and about 22, and wherein the alkyl group is selected from the group consisting of a methyl group, an ethyl group, propyl group, an isopropyl group, a butyl group, a tertiary-butyl group, a pentyl group, a neopentyl group, a hexyl group, an octyl group, a decyl group, a dodecyl group, and combinations thereof.

11. The method of claim 9, wherein the aryl group includes a phenyl group.

12. The method of claim 9, wherein the bicycloalkyl and cycloalkyl groups each include ring carbon atoms in a range between about 3 and about 12, wherein the bicycloalkyl and cycloalkyl groups each include no more than about 50 carbon atoms, and wherein the bicycloalkyl and cycloalkyl group is each independently selected from the group consisting of a cyclobutyl group, a cyclopentyl group, a cyclohexyl group, a methylcyclohexyl group, a cycloheptyl group, and combinations thereof.

13. The method of claim 9, wherein the aralkyl group includes carbon atoms in a range between about 7 and about 14, and wherein the aralkyl group comprises a benzyl group, a phenylbutyl group, a phenylpropyl group, a phenylethyl group, or combinations thereof.

14. The method of claim 1, wherein the starting silane comprises tetramethoxysilane, tetraethoxysilane, tetraisopropoxysilane, or combinations thereof.

15. The method of claim 1, wherein the starting silane comprises tetraphenoxysilane, dimethoxydiphenoxysilane, or combinations thereof.

16. The method of claim 1, wherein the product silane is selected from the group consisting of methyltrimethoxysilane, ethyltriethoxysilane, propyltripropoxysilane, methyldimethoxysilane, ethyldiethoxysilane, propyldipropoxysilane, and combinations thereof.

17. The method of claim 1, wherein the reacting includes reacting in a reactor comprises a fixed bed reactor, a stirred bed reactor, and a fluidized bed reactor.

18. The method of claim 1, wherein the reacting includes reacting in a mode comprising a continuous mode, a batch mode, and a semi-continuous mode.

19. A method for forming at least one product silane, comprising endothermically reacting a transition metal hydride with a starting silane in a presence of a catalyst and at a temperature in a range between about 350° C. and about 600° C., wherein the starting silane comprises tetramethoxysilane, tetraethoxysilane, tetraisopropoxysilane, or combinations thereof.

20. A method for forming at least one product silane, comprising endothermically reacting a transition metal hydride with a starting silane in a presence of a catalyst and at a temperature in a range between about 350° C. and about 600° C., wherein the starting silane comprises tetraphenoxysilane, dimethoxydiphenoxysilane, or combinations thereof.

* * * * *